(12) United States Patent  (10) Patent No.: US 8,282,800 B2
Rowell et al.  (45) Date of Patent: Oct. 9, 2012

(54) HYDROLYSIS-RESISTANT POLYACRYLAMIDE GELS

(75) Inventors: Craig Rowell, Albany, CA (US); Cory Panattoni, Winters, CA (US); Thomas R. Berkelman, Oakland, CA (US); Sean Cater, Oakland, CA (US); Shane Petersen, Fairfield, CA (US); Lee Olech, Pinole, CA (US); Xuemei Yang, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 601 days.

(21) Appl. No.: 12/552,104

(22) Filed: Sep. 1, 2009

(65) Prior Publication Data

US 2010/0051462 A1 Mar. 4, 2010

Related U.S. Application Data

(60) Provisional application No. 61/093,622, filed on Sep. 2, 2008.

(51) Int. Cl.
*G01N 27/447* (2006.01)

(52) U.S. Cl. .................. 204/468; 204/456; 204/606

(58) Field of Classification Search .................. 204/456, 204/468, 606
See application file for complete search history.

(56) References Cited

U.S. PATENT DOCUMENTS

| | | | | | |
|---|---|---|---|---|---|
| 4,522,742 | A | * | 6/1985 | Lee et al. ................. | 252/301.16 |
| 4,654,132 | A | * | 3/1987 | Takagi et al. ................. | 204/468 |
| 5,314,595 | A | * | 5/1994 | Fuller ........................... | 204/468 |
| 5,447,612 | A | | 9/1995 | Bier et al. | |
| 5,993,627 | A | * | 11/1999 | Anderson et al. ............. | 204/456 |
| 6,582,574 | B1 | * | 6/2003 | Liu et al. ....................... | 204/456 |
| 6,726,821 | B1 | * | 4/2004 | Suzuki .......................... | 204/456 |

FOREIGN PATENT DOCUMENTS

EP 0808853 A2 11/1997

OTHER PUBLICATIONS

Orr et al, Analytical Biochemistry 45, pp. 68-85, 1972.*
Chang et al, Analytical Biochemistry 97, pp. 36-42, 1979.*

* cited by examiner

*Primary Examiner* — Kaj K Olsen
(74) *Attorney, Agent, or Firm* — Kilpatrick Townsend & Stockton LLP.; M. Henry Heines

(57) ABSTRACT

Polyacrylamide gels that offer high resolution in protein separations and are more stable relative to hydrolysis than conventional polyacrylamide gels that rely on Tris or Tris-Bis as buffering agents are made by incorporating triethanolamine in place of most or all of the Tris or Tris-Bis.

54 Claims, 1 Drawing Sheet

HYDROLYSIS-RESISTANT POLYACRYLAMIDE GELS

CROSS-REFERENCE TO RELATED APPLICATION

This application claims the benefit of U.S. Provisional Patent Application No. 61/093,622, filed Sep. 2, 2008, the contents of which are incorporated herein by reference.

BACKGROUND OF THE INVENTION

The wide use of polyacrylamide gel electrophoresis ("PAGE") in research, in diagnostics studies, and in biochemistry laboratories in general is due in large part to the optical transparency and electrical neutrality of polyacrylamide gels, as well as the flexibility and adaptability of polyacrylamide gels to a wide range of molecular sizes of the species to be separated in the gel. This flexibility arises from the manufacturer's ability to control the porosity of the gel by varying the concentration of the acrylamide monomer and the proportion of the crosslinking agent, generally bis-acrylamide, relative to the monomer. PAGE is particularly useful for protein separations when sodium dodecyl sulfate (SDS) is incorporated into the gel with an appropriate buffer. Commonly used buffers are tris(hydroxymethyl)aminomethane ("Tris") and bis(2-hydroxyethyl)amino-tris(hydroxymethyl)methane ("Bis-Tris"). Prominent among polyacrylamide gels for protein separations is one originally described by Laemmli, U.K., Nature 227: 680 (1970), which contains Tris-HCl as a buffer at pH 8.8. Unfortunately, the high pH causes these gels to hydrolyze over time, even when the gels are refrigerated. Hydrolysis reduces the migration distance of individual proteins and lowers the resolution of the protein bands. If the pH is lowered in an attempt to avert hydrolysis, the separation of proteins by the gel is less clear and useful analyses of protein mixtures can no longer be obtained.

SUMMARY OF THE INVENTION

It has now been discovered that a polyacrylamide gel that is resistant to hydrolysis, even during long-teen storage, and yet able to separate and resolve proteins under electrophoretic conditions is achieved by substituting triethanolamine for Tris and Bis-Tris. Thus, in certain embodiments of the invention, the level of Tris, Bis-Tris, or both are reduced considerably relative to the prior art gels, while in others both Tris and Bis-Tris are absent entirely. Additional species such as ampholytes, conjugate ampholytes, stabilizers, pH modifiers, band-sharpening agents, and further buffers are also included as optional components in certain embodiments of the invention, as discussed below. The use of triethanolamine can produce an improvement in the band resolution in general, upon the use of the gel both on the day of preparation and over the course of long-term storage. The inclusion of triethanolamine can also allow the gel to be run at high voltages without the loss of band resolution that typically occurs with gels of the prior art. A further advantage of the use of triethanolamine is its ability to function effectively upon buffering of the gel solution to neutrality. A still further advantage is that the triethanolamine-containing gels of this invention can be used with a wide range of running buffers, including running buffers with different cations than those in the gels, with no significant loss of resolution. The gels can thus be used with a Tris-glycine running buffer.

The expression "resistant to hydrolysis during long-term storage" as used in this specification denotes that the gel remains capable of producing an analytically useful electrophoretic separation of proteins after storage for periods of time in excess of one day, preferably in excess of three days, more preferably seven days or more, still more preferably one month or more, and still more preferably six months or more, under storage conditions common to the use of pre-cast electrophoresis gels. This invention is applicable to gels of any size or shape, including both tube gels and slab gels, as well as combinations of stacking and resolution gels. This invention is also applicable to gels in microfluidic devices.

DETAILED DESCRIPTION OF THE INVENTION AND PREFERRED EMBODIMENTS

Figure 1:
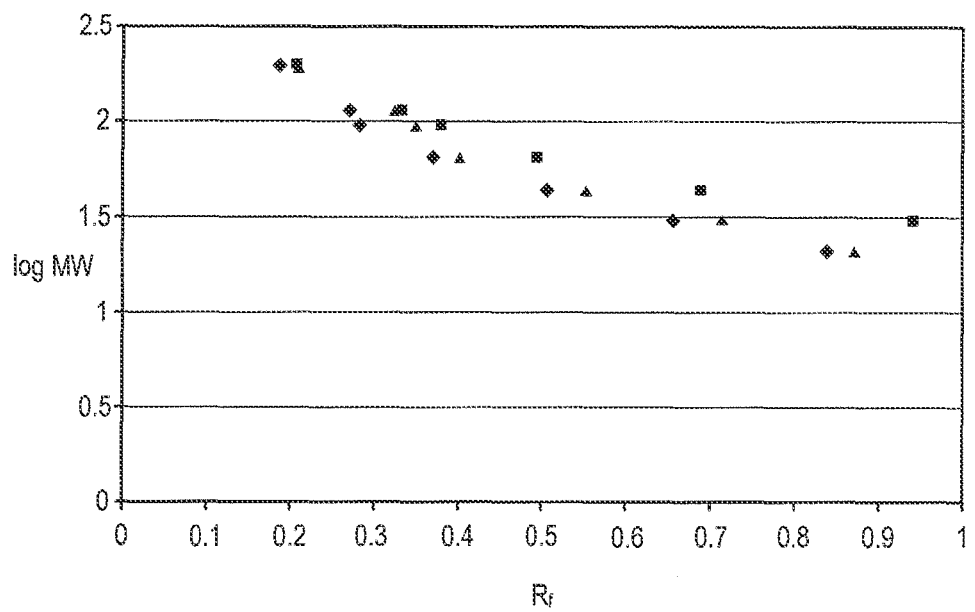
FIG. 1 is a Laemmli plot comparing the electrophoretic performance of two gels within the scope of the present invention containing asparagine at different levels, with a gel containing 10 mole % Tris-HCl.

Polyacrylamide gels are formed by the polymerization of acrylamide monomer and bis-acrylamide as a crosslinker in the presence of a polymerization catalyst according to methods well known in the art, and the present invention is applicable to polyacrylamide gels of a wide range of porosities. As also known in the art, the porosities can be controlled by varying the total acrylamide concentration as well as the proportion of bis-acrylamide to total acrylamides. According to common usage in the art, the total acrylamide (i.e., total monomer, including crosslinker) concentration is expressed in weight percent and referred to by the symbol T, while the proportion of crosslinker to total monomer is likewise expressed in weight percent and referred to by the symbol C. The values of neither T nor C are critical to the present invention, although in most applications, T will range from about 4% to about 25%, preferably from about 8% to about 15%, and C will range from about 2% to about 10%, preferably from about 2.5% to about 5%. Examples of catalysts known in the art to promote the polymerization are ammonium persulfate, N,N'-tetramethylenediamine (TEMED), riboflavin, and 3-dimethylamino-propionitrile, all used in catalytic mounts that are readily apparent to those skilled in the art.

In accordance with the invention, triethanolamine is incorporated in the monomer solution so that the triethanolamine is included in the gel thus formed. Triethanolamine can also be included in the running buffer, but this is not critical to goal of this invention in preserving the stability of the gel during storage over a period of days, weeks, or months. In the monomer solution, the concentration of triethanolamine can vary, although best results in most cases will be achieved with a concentration within the range of about 0.01 mol/L (1.5% by weight) to about 0.25 mol/L (37.3% by weight). A preferred range is about 0.05 mole/L (50 mM) to about 0.2 mol/L (200 mM), a more preferred range is about 0.075 mole/L (75 mM) to about 0.15 mol/L (150 mM). (In this specification and the claims that follow, the concentration of triethanolamine and of other components of the gel are at times expressed in mM of the gel. This is understood to be equivalent to mM of the monomer solution from which the gel was cast.)

A further component of the gel that present in preferred embodiments of the invention is one or more ampholytes, a notable example of which is glycine, and one or more conjugate ampholytes. Suitable conjugate ampholytes are those with a $pK_a$ within the range of 8.3 to 9.6 and are typically amino acids. Examples are asparagine, taurine, threonine, serine, and histidine. When included, glycine is preferably present at a concentration within the range of about 0.05 mol/L (50 mM) to about 0.5 mol/L (500 mM), and the conjugate ampholyte is preferably present at a proportion relative to the ampholyte (e.g., glycine) of from about 0.1 mole percent to about 65 mole percent, preferably from about 20 mole percent to about 60 mole percent. (A mole percent representing a proportion of the conjugate ampholyte relative to the ampholyte is used herein to mean the number of moles of the conjugate ampholyte divided by the total number of moles of ampholyte and conjugate ampholyte, multiplied by 100.) In certain embodiments, a weak acid or combination of two or more weak acids is included as well. Examples are citric acid, glycolic acid, maleic acid, phosphoric acid, acetic acid, and boric acid. When present, the concentration of weak acid or acids will preferably be within the range of about 0.01 mol/L (10 mM) to about 0.50 mol/L (500 mM), and most preferably from about 0.03 mol/L (30 mM) to about 0.10 mol/L (100 mM). Citric acid, maleic acid, and glycolic acid are preferred, with glycolic acid the most preferred. A further optional additive is a neutral salt for further band resolution, particularly over long-term storage. Examples of suitable salts are sodium chloride, sodium sulfate, sodium phosphate, potassium chloride, and potassium phosphate. When present, the concentration of the neutral salt will preferably be within the range of about 0.01 mol/L (10 mM) to about 0.50 mol/L (500 mM), and most preferably from about 0.03 mol/L (30 mM) to about 0.10 mol/L (100 mM). As in typical polyacrylamide gel preparations of the prior art, the pH of the monomer solution can be adjusted to the desired range with a suitable acid, examples of which are hydrochloric acid, sulfuric acid, acetic acid, boric acid, and phosphoric acid. As needed, the pH can be adjusted to a value within the range of 6.4 to 9.0. A pH range of 6.4 to 7.0 is preferred.

As further noted above, the gels of the present invention contain little or no Tris or Bis-Tris. When present, the Tris or Bis-Tris constitutes 0.3 mM or less of the gel, preferably from about 0.03 mM to about 0.3 mM. In certain embodiments, one or both of these two buffers is absent entirely, or is at least substantially absent, i.e., no more than trace amounts of these buffers are present, and any amounts that are present will be small enough to have no detectable effect on the storage stability of the gels.

Electrophoretic separations performed on the gels described herein is conducted under conventional conditions of temperature, voltage, and time, using a wide range of sample buffers and running buffers and other materials used in conjunction with the gels. Electrophoresis on slab gels is preferred, and the samples can be loaded onto the gels in any conventional manner. The gels of the invention do however permit the separations to be performed at higher voltages than are typically used, allowing the separations to be performed in shorter periods of time with no loss in resolution. Gels ranging in length from about 6 cm to about 30 cm are commonly used, and the voltage can range from about 50V to about 600V. When high voltages are used, the range can be about 350 volts or higher, and preferably from about 400 volts to about 600 volts. On a volts-per-centimeter basis, the range can be from about 1 V/cm to about 100 V/cm, or for high voltages, preferably from about 50 V/cm to about 100 V/cm.

While the experiments reported in the examples that follow were performed in slab gels, gels in accordance with the invention can also reside in microfluidic devices and still demonstrate the benefits described herein. In microfluidic devices, the gels will reside in microchannels that are 500 microns or less, and preferably 100 microns or less, in diameter (or in the longest cross-sectional dimension of the channel).

In the following examples, a standard protein mixture was separated by electrophoresis in a variety of gels of varying compositions and after different storage times of the gels. For Examples 1 through 8, the protein mixture contained myosin, beta-galactosidase, bovine serum albumin, ovalbumin, carbonic anhydrase, soybean trypsin inhibitor, lysosyme, and aprotinin. The sample buffer in each case consisted of 62.5 mM Tris-HCl, 2% sodium dodecyl sulfate, 25% glycerol, and 0.01% bromophenol blue, at pH 6.8. The running buffer in each case consisted of 25 mM Tris, 192 mM glycine, and 0.1% sodium dodecyl sulfate, at pH 8.3. Separations were performed at a constant voltage of 200V for 30-50 minutes. All percents that are not otherwise indicated are by weight.

EXAMPLE 1

This example compares the performance of polyacrylamide gels prepared with triethanolamine within the scope of the invention with a polyacrylamide gel prepared with Tris-HCl and thus outside the scope of the invention in electrophoretic separations. The separations were performed the same day the gels were prepared.

A series of polyacrylamide gels were cast in slab gel electrophoresis cassettes using a 10% aqueous acrylamide/bis-acrylamide solution (T=10%) of which the bis-acrylamide constituted 2.6% of the monomer mixture (C=2.6%). Also included in the casting solutions were 5% glycerol and sufficient HCl to adjust the pH to 6.4-6.5. The control solution further included 10 mole % Tris-HCl, while the test solutions included 75 mM triethanolamine plus either 82.6 mM asparagine, 82.6 mM glycyl glycine, or 82.6 mM glycyl glycine in combination with 100 mM MES. None of the test solutions contained Tris-HCl. A standard protein mixture was run on all gels, using a Ready Gel cassette for the control gel and two test gels, one containing glycyl glycine and one containing asparagine, and a Mini-Protean III Cell for two further test gels, one containing glycyl glycine in combination with MES, and one containing asparagine. The cassette and cell are standard items sold by Bio-Rad Laboratories, Inc., Hercules, Calif., USA.

A comparison of the resulting electropherograms showed that the gels prepared with triethanolamine produced band resolution and separation time similar to those of the gel prepared with Tris-HCl. The results also showed that the gel containing both triethanolamine and asparagine produced a band distribution most similar to that of the Tris-HCl-containing gel.

EXAMPLE 2

This example illustrates the performance of polyacrylamide gels within the scope of the invention containing asparagine and glycine, each at various concentrations. Electrophoretic separations were performed on the gels the same day the gels were prepared.

The monomer compositions of the gel solutions were T=10% and C=2.6%, the same as in Example 1, and the remaining components of the solutions were as follows, where TEA denotes triethyanolamine, ASN denotes asparagine, and GLY denotes glycine:

| Gel | Composition (in addition to acrylamide/bis-acrylamide) |
|---|---|
| (A) | 150 mM TEA; 86.5 mM ASN |
| (B) | 150 mM TEA; 5 mM ASN |
| (C) | 150 mM TEA; 5 mM ASN; 5 mM GLY |
| (D) | 150 mM TEA; 5 mM ASN; 12.5 mM GLY |
| (E) | 150 mM TEA; 5 mM ASN; 50 mM GLY |
| (F) | 150 mM TEA; 5 mM ASN; 75 mM GLY |
| (G) | 150 mM TEA; 5 mM ASN; 100 mM GLY |

The standard protein mixture was run on all gels and a comparison of the resulting electropherograms revealed that there was no loss in band resolution and distribution by using the lower rather than the higher asparagine concentration, and that some improvement in band resolution was achieved as the glycine concentration increased.

FIG. 1 is a Laemmli plot, i.e., a plot of the logarithm of the molecular weights of the proteins vs. the relative mobility $R_f$ (the ratio of the migration distance of the proteins to the migration distance of a leading marker dye, i.e., to the resolving length of the gel), for gels A and B and for a Laemmli gel made with 10% Tris-HCl (10 mole % Tris, adjusted to pH 8.8 with HCl, according to Laemmli, U.K., *Nature* 227: 680 (1970)) in place of the triethanolamine, asparagine, and glycine. The points in this plot are as follows:

| Symbol | Gel Composition (in addition to monomers) |
|---|---|
| diamonds | 150 mM TEA; 5 mM ASN |
| triangles | 150 mM TEA; 86.5 mM ASN |
| squares | 10 mole % Tris-HCl |

The plot indicates that both triethanolamine-containing gels gave performances comparable to that of Tris-HCl.

EXAMPLE 3

This example is a further illustration of the effects of using triethanolamine in combination with varying the concentrations of asparagine and glycine, all within the scope of the invention and without Tris-HCl. Tests were performed on the gels the same day the gels were prepared.

Using the same monomer compositions as those of Example 1, the remaining components of the solutions were as follows (using the abbreviations indicated above):

| Gel | Composition (in addition to acrylamide/bis-acrylamide) |
|---|---|
| (A) | 75 mM TEA; 83 mM ASN |
| (B) | 75 mM TEA; 12.5 mM ASN; 100 mM GLY |
| (C) | 75 mM TEA; 25 mM ASN; 100 mM GLY |
| (D) | 75 mM TEA; 50 mM ASN; 100 mM GLY |
| (E) | 75 mM TEA; plus 75 mM ASN; 100 mM GLY |

The standard protein mixture was run on all gels and a comparison of the resulting electropherograms revealed that band resolution and distribution was achieved in all cases.

EXAMPLE 4

This example is a shelf life study of polyacrylamide gels within the scope of the invention in an accelerated test. The gels were formed from acrylamide/bis-acrylamide at T=10% and C=2.6% with 150 mM triethanolamine, 5 mM asparagine, and either 50 mM or 75 mM glycine, and the accelerated test was performed by storing the gels at 37° C. (one day at 37° C. is equivalent to one month at the typical storage temperature of 4° C.).

The standard protein mixture was run on all gels after 6 days, 10 days, and 12 days of storage, and the electropherograms indicated that viable separations were obtained in each case, with an indication that the higher glycine concentrations resulted in improved gel stability.

EXAMPLE 5

This example is a further shelf life study of polyacrylamide gels within the scope of the invention, again in an accelerated test, using a variety of buffers. The gels were formed from acrylamide/bis-acrylamide at T=10% and C=2.6% with the compositions shown below. The abbreviations used are as follows: TEA=triethanolamine; ASN=asparagine; AMME=2-amino-2-methyl-1.3 propanediol (AMMEDIOL); IMM=imidazole; ADA=N-(2-acetamido)-iminodiacetic acid; GLY=glycine.

| Gel | Composition (in addition to acrylamide/bis-acrylamide) |
|---|---|
| (A) | 100 mM TEA; 100 mM ASN; 40 mM AMME; 200 mM GLY |
| (B) | 100 mM TEA; 100 mM ASN; 40 mM IMM; 200 mM GLY |
| (C) | 100 mM TEA; 100 mM ASN; 40 mM ADA; 200 mM GLY |
| (D) | 150 mM TEA; 165 mM ASN; 40 mM ADA; 300 mM GLY |
| (E) | 150 mM TEA; 165 mM ASN; 40 mM ADA; 400 mM GLY |

The gels were stored at 37° C., and the standard protein mixture was run on gels the day the gels were prepared, on gels stored for 6 days, and on gels stored for 12 days. The electropherograms indicated that viable separations were obtained in each case, with the gels containing AMMEDIOL producing separations as clear as those produced with the gels containing ADA.

EXAMPLE 6

This example illustrates the performance of polyacrylamide gels prepared with triethanolamine (TEA) in combination with three alternative buffers, N-(2-acetamido)-iminodiacetic acid (ADA), maleic acid, and citric acid. The gels were formed from acrylamide/bis-acrylamide at T=10% and C=2.6% with 125 mM TEA, 132.5 mM asparagine (ASN), 250 mM glycine (GLY), and either 40 mM ADA, 40 mM citric acid, 20 mM maleic acid, or 40 mM maleic acid, the same standard protein mixture used in the preceding examples was used, and electrophoresis of the standard protein mixture was performed in the MiniProtean III electrophoresis cell at 200V on the same day the gels were prepared.

Figure 2:
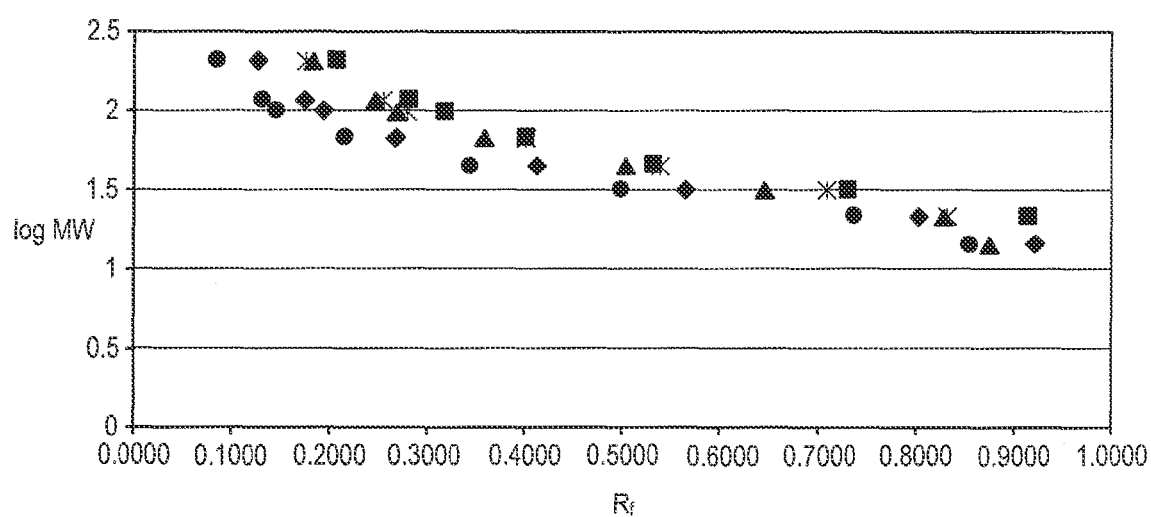
FIG. 2 is a Laemmli plot comparing the electrophoretic performance of four gels within the scope of the present invention containing a variety of weak acid buffers with a gel containing 10 mole % Tris-HCl.

FIG. 2 is a Laemmli plot of the molecular weights of the proteins vs. the relative mobility $R_f$ for each of the four gels plus a Laemmli gel (10 mole % Tris-HCl, pH 8.8). The points in this plot are as follows:

| Symbol | Gel Composition (in addition to acrylamide/bis-acrylamide) |
|---|---|
| diamonds | 125 mM TEA; 132.5 mM ASN; 250 mM GLY; 20 mM maleic acid; |
| triangles | 125 mM TEA; 132.5 mM ASN; 250 mM GLY; 40 mM citric acid; |
| asterisks | 125 mM TEA; 132.5 mM ASN; 40 mM ADA; 250 mM GLY |
| circles | 125 mM TEA; 132.5 mM ASN; 250 mM GLY; 40 mM |

-continued

| Symbol | Gel Composition (in addition to acrylamide/bis-acrylamide) |
|---|---|
| | maleic acid; |
| squares | 10 mole % Tris-HCl (Laemmli) |

The plot shows that the curves for each of the gels closely follow the curve representing the 10 mole % Tris-HCl gel, indicating that all are viable gels for electrophoresis.

EXAMPLE 7

This example is a shelf life study, illustrating the effects of the inclusion of sodium chloride in the gel buffer system in combination with N-(2-acetamido)iminodiacetic acid (ADA). Gels were formed from acrylamide/bis-acrylamide at T=10% and C=2.6% with 125 mM triethanolamine (TEA), 132.5 mM asparagine (ASN), 250 mM glycine (GLY), and 40 mM ADA, and either no NaCl, 10 mM NaCl, or 50 mM NaCl. Gels were either used on the day they were prepared or stored at 37° C. for twelve days. Electrophoresis was performed in the Mini-Protean III electrophoresis cell.

A Laemmli plot was prepared of the molecular weights of the proteins vs. the relative mobility $R_f$ for each of the four gels plus a gel prepared with 10 mole % Tris-HCl. The gels used and the number of days of storage under the accelerated temperature condition were as follows:

Gel Composition (in Addition to Monomers) and Length of Storage
  125 mM TEA; 132.5 mM ASN; 40 mM ADA; 250 mM GLY; zero NaCl—twelve days
  125 mM TEA; 132.5 mM ASN; 40 mM ADA; 250 mM GLY; 10 mM NaCl—zero days
  125 mM TEA; 132.5 mM ASN; 40 mM ADA; 250 mM GLY; 10 mM NaCl—twelve days
  125 mM TEA; 132.5 mM ASN; 40 mM ADA; 250 mM GLY; 50 mM NaCl—zero days
  125 mM TEA; 132.5 mM ASN; 40 mM ADA; 250 mM GLY; 50 mM NaCl—twelve days
  10 mole % Tris-HCl—zero days The plot showed that the curves for each gel closely follows the 10 mole % Tris-HCl curve, indicating that all are viable gels for electrophoresis and that all are stable over the 12-day accelerated test.

EXAMPLE 8

This example is a shelf life study, illustrating the effects of the inclusion of citric acid in the triethanolamine buffer system at various concentrations. Gels were formed from acrylamide/bis-acrylamide at T=10% and C=2.6% with 125 mM TEA, 132.5 mM ASN, 250 mM GLY, 10-40 mM citric acid, and either no NaCl or 50 mM NaCl. Gels were either used on the day they were prepared or stored at 37° C. for six or twelve days and then used. For electrophoresis, the same standard protein mixture used in the preceding examples was used, and electrophoresis was performed in the MiniProtean III electrophoresis cell at 200V.

The electropherograms showed that while the 20 mM and 40 mM citric acid gels displayed a significant loss of resolution at day 12 (under the accelerated test condition), the 10 mM citric acid gel did maintain good band resolution through day 12, and the gel containing 40 mM citric acid and 50 mM NaCl likewise maintained good band resolution through day 12.

EXAMPLE 9

This example is a further accelerated shelf life study, comparing a polyacrylamide gel in accordance with the invention with a polyacrylamide gel prepared in a Laemmli buffer. Both gels had a T value of 10% and a C value of 2.6%. The polyacrylamide gel of the invention was prepared in a buffer solution whose composition was 50 mM triethanolamine, 100 mM glycine, 100 mM taurine, 01 mM Tris-HCl, and 49 mM glycolic acid. The pH at 30 minutes after preparation of the monomer solution was 6.5. The Laemmli buffer consisted of 60 mM Tris-HCl, 10% glycerol, 2% SDS, and 5% β-mercaptoethanol, with HCl to adjust the pH to about 8.8.

Cassettes in which the gels were cast were stored at 37° C. for various lengths of time, with one gel of each type being used the same day it was cast. The lengths of storage time were thus zero days, one day, two days, three days, six days, twelve days, and eighteen days. A selection of different samples was then run on each gel with different samples in different lanes of the same gel, each gel containing ten lanes. The samples included two standard protein mixtures available from Bio-Rad Laboratories, Inc. Hercules, Calif., USA: "Precision Plus Protein Standard," and broad-range "Natural Protein Standard." The protein mixture *E. coli* lysate and mouse serum were also run.

In the Laemmli gels, deterioration in the form of blurred bands was evident after three days of storage, whereas in the gels of the invention, sharp bands were obtained on gels stored for as much as eighteen days.

EXAMPLE 10

This example is a real-time shelf life study with storage of the gels at 4° C. for ten months. A polyacrylamide gel in accordance with the invention was compared with a polyacrylamide gel prepared in a buffer containing Tris-HCl and taurine but no triethanolamine. Both gels had a C value of 2.6%, and the gel of the invention had a T value of 12% while the gel prepared in the Laemmli buffer was a gradient gel with a T value increasing from 4% to 20% in the direction of protein migration. The polyacrylamide gel of the invention was prepared in a buffer solution whose composition was 50 mM triethanolamine, 100 mM glycine, 100 mM taurine, 0.1 mM Tris-HCl, and 49 mM glycolic acid. The pH at 30 minutes after preparation of the monomer solution was 6.5. The comparative buffer consisted of 75 mM Tris-HCl and 200 mM taurine at pH 6.5.

Cassettes in which the gels were cast were stored at 4° C. for ten months, with one gel of each type being used the same day it was cast. The samples run on each gel included the two standard protein from Bio-Rad Laboratories, Inc., identified above, in all gels, plus the *E. coli* lysate in the ten-month gels. Band sharpness and relative migration at ten months were approximately the same with both gel chemistries, although shadow bands were noted in the ten-month gel prepared in the Laemmli buffer, and yellowing of the dye front and distortion was observed in the lanes of the gel prepared in the Laemmli buffer for the broad range standard.

This example also illustrates the unusually favorable resolving power of the gels of the invention when run at elevated voltage. Runs were performed on gradient gels of the two chemistries above (except that the trisethanolamine-taurine gel was prepared with HCl rather than glycolic acid), both gels being of a 4% to 12% gradient, each gel being _____ in length. These runs were performed at 500 volts (as compared to 100-200 volts used in typical electrophoresis separations) for 9.5 minutes on gels that had been stored for nine days at 37° C. using the broad range standard as a sample. The triethanolamine-taurine gel of the invention produced very good resolution and the buffer temperature displayed normal behavior. The Tris-taurine gel, y contrast, produced poor resolution with blurred bands, and the buffer temperature was elevated during the run.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A polyacrylamide gel comprising crosslinked polyacrylamide in a buffer solution comprising triethanolamine, said gel having about 0.03 mM to about 0.3 mM of tris(hydroxymethyl)aminomethane and being devoid of bis(2-hydroxyethyl)amino-tris(hydroxymethyl)methane.

2. The polyacrylamide gel of claim 1 wherein said triethanolamine constitutes from about 10 mM to about 250 mM of said gel.

3. The polyacrylamide gel of claim 1 wherein said triethanolamine constitutes from about 75 mM to about 150 mM of said gel.

4. The polyacrylamide gel of claim 1 further comprising an ampholyte.

5. The polyacrylamide gel of claim 4 wherein said ampholyte is glycine at a concentration of from about 50 mM to about 500 mM.

6. The polyacrylamide gel of claim 5 further comprising a conjugate ampholyte at a proportion of from about 0.1 mole percent to about 65 mole percent relative to said glycine.

7. The polyacrylamide gel of claim 6 wherein said conjugate ampholyte is at a proportion of from about 20 mole percent to about 60 mole percent relative to said glycine.

8. The polyacrylamide gel of claim 6 wherein said conjugate ampholyte is a member selected from the group consisting of asparagine, taurine, threonine, serine, and histidine.

9. The polyacrylamide gel of claim 6 wherein said conjugate ampholyte is taurine and is at a proportion of from about 20 mole percent to about 60 mole percent relative to said glycine.

10. The polyacrylamide gel of claim 5 further comprising a weak acid at a concentration of from about 10 mM to about 500 mM.

11. The polyacrylamide gel of claim 1 wherein said gel has a polyacrylamide concentration of from about 4% to about 25% by weight, with a crosslinker proportion of from about 2% to about 10% by weight.

12. A polyacrylamide gel comprising crosslinked polyacrylamide in a buffer solution comprising triethanolamine, said gel having about 0.03 mM to about 0.3 mM of bis(2-hydroxyethyl)-amino-tris(hydroxymethyl)methane and being devoid of tris(hydroxymethyl)aminomethane.

13. The polyacrylamide gel of claim 12 wherein said triethanolamine constitutes from about 10 mM to about 250 mM of said gel.

14. The polyacrylamide gel of claim 12 wherein said triethanolamine constitutes from about 75 mM to about 150 mM of said gel.

15. The polyacrylamide gel of claim 12 further comprising an ampholyte.

16. The polyacrylamide gel of claim 15 wherein said ampholyte is glycine at a concentration of from about 50 mM to about 500 mM.

17. The polyacrylamide gel of claim 16 further comprising a conjugate ampholyte at a proportion of from about 0.1 mole percent to about 65 mole percent relative to said glycine.

18. The polyacrylamide gel of claim 17 wherein said conjugate ampholyte is at a proportion of from about 20 mole percent to about 60 mole percent relative to said glycine.

19. The polyacrylamide gel of claim 17 wherein said conjugate ampholyte is a member selected from the group consisting of asparagine, taurine, threonine, serine, and histidine.

20. The polyacrylamide gel of claim 17 wherein said conjugate ampholyte is taurine and is at a proportion of from about 20 mole percent to about 60 mole percent relative to said glycine.

21. The polyacrylamide gel of claim 16 further comprising a weak acid at a concentration of from about 10 mM to about 500 mM.

22. The polyacrylamide gel of claim 15 wherein said gel has a polyacrylamide concentration of from about 4% to about 25% by weight, with a crosslinker proportion of from about 2% to about 10% by weight.

23. A polyacrylamide gel comprising crosslinked polyacrylamide in a buffer solution comprising triethanolamine, said gel having about 0.03 mM to about 0.3 mM of tris(hydroxymethyl)-aminomethane and about 0.03 mM to about 0.3 mM of bis(2-hydroxyethyl)amino-tris(hydroxymethyl)methane.

24. The polyacrylamide gel of claim 23 wherein said triethanolamine constitutes from about 10 mM to about 250 mM of said gel.

25. The polyacrylamide gel of claim 23 wherein said triethanolamine constitutes from about 75 mM to about 150 mM of said gel.

26. The polyacrylamide gel of claim 23 further comprising an ampholyte.

27. The polyacrylamide gel of claim 26 wherein said ampholyte is glycine at a concentration of from about 50 mM to about 500 mM.

28. The polyacrylamide gel of claim 27 further comprising a conjugate ampholyte at a proportion of from about 0.1 mole percent to about 65 mole percent relative to said glycine.

29. The polyacrylamide gel of claim 28 wherein said conjugate ampholyte is at a proportion of from about 20 mole percent to about 60 mole percent relative to said glycine.

30. The polyacrylamide gel of claim 28 wherein said conjugate ampholyte is a member selected from the group consisting of asparagine, taurine, threonine, serine, and histidine.

31. The polyacrylamide gel of claim 28 wherein said conjugate ampholyte is taurine and is at a proportion of from about 20 mole percent to about 60 mole percent relative to said glycine.

32. The polyacrylamide gel of claim 27 further comprising a weak acid at a concentration of from about 10 mM to about 500 mM.

33. The polyacrylamide gel of claim 23 wherein said gel has a polyacrylamide concentration of from about 4% to about 25% by weight, with a crosslinker proportion of from about 2% to about 10% by weight.

34. A method for separating a mixture of proteins by electrophoresis, said method comprising (i) loading a gel with a sample of said mixture wherein said gel comprises crosslinked polyacrylamide in a buffer solution comprising triethanolamine, said gel having about 0.03 mM to about 0.3 mM of tris(hydroxymethyl)aminomethane and being devoid of bis(2-hydroxyethyl)amino-tris(hydroxymethyl)methane, and (ii) imposing a voltage across said gel to cause said proteins to migrate through said gel at differential rates until separated into bands within said gel.

35. The method of claim 34 wherein said triethanolamine constitutes from about 10 mM to about 250 mM of said gel.

36. The method of claim 34 wherein said gel further comprises glycine at a concentration of from about 50 mM to about 500 mM.

37. The method of claim 34 wherein said gel further comprises glycine at a concentration of from about 50 mM to about 500 mM and a conjugate ampholyte at a proportion of from about 20 mole percent to about 60 mole percent relative to said glycine.

38. The method of claim 34 wherein said triethanolamine constitutes from about 10 mM to about 250 mM of said gel, and said gel further comprises glycine at a concentration of from about 50 mM to about 500 mM, a conjugate ampholyte at a proportion of from about 20 mole percent to about 60 mole percent relative to said glycine, and a weak acid at a concentration of from about 10 mM to about 500 mM.

39. The method of claim 34 wherein said voltage is at least about 350 volts.

40. The method of claim 34 wherein said voltage is from about 400 volts to about 600 volts.

41. A method for separating a mixture of proteins by electrophoresis, said method comprising (i) loading a gel with a sample of said mixture wherein said gel comprises crosslinked polyacrylamide in a buffer solution comprising triethanolamine, said gel having about 0.03 mM to about 0.3 mM of bis(2-hydroxyethyl)amino-tris(hydroxymethyl)aminomethane and being devoid of tris(hydroxymethyl)methane, and (ii) imposing a voltage across said gel to cause said proteins to migrate through said gel at differential rates until separated into bands within said gel.

42. The method of claim 41 wherein said triethanolamine constitutes from about 10 mM to about 250 mM of said gel.

43. The method of claim 41 wherein said gel further comprises glycine at a concentration of from about 50 mM to about 500 mM.

44. The method of claim 41 wherein said gel further comprises glycine at a concentration of from about 50 mM to about 500 mM and a conjugate ampholyte at a proportion of from about 20 mole percent to about 60 mole percent relative to said glycine.

45. The method of claim 41 wherein said triethanolamine constitutes from about 10 mM to about 250 mM of said gel, and said gel further comprises glycine at a concentration of from about 50 mM to about 500 mM, a conjugate ampholyte at a proportion of from about 20 mole percent to about 60 mole percent relative to said glycine, and a weak acid at a concentration of from about 10 mM to about 500 mM.

46. The method of claim 41 wherein said voltage is at least about 350 volts.

47. The method of claim 41 wherein said voltage is from about 400 volts to about 600 volts.

48. A method for separating a mixture of proteins by electrophoresis, said method comprising (i) loading a gel with a sample of said mixture wherein said gel comprises crosslinked polyacrylamide in a buffer solution comprising triethanolamine, said gel having about 0.03 mM to about 0.3 mM of tris(hydroxymethyl)aminomethane and about 0.03 mM to about 0.3 mM of bis(2-hydroxyethyl)amino-tris(hydroxymethyl)methane, and (ii) imposing a voltage across said gel to cause said proteins to migrate through said gel at differential rates until separated into bands within said gel.

49. The method of claim 48 wherein said triethanolamine constitutes from about 10 mM to about 250 mM of said gel.

50. The method of claim 48 wherein said gel further comprises glycine at a concentration of from about 50 mM to about 500 mM.

51. The method of claim 48 wherein said gel further comprises glycine at a concentration of from about 50 mM to about 500 mM and a conjugate ampholyte at a proportion of from about 20 mole percent to about 60 mole percent relative to said glycine.

52. The method of claim 48 wherein said triethanolamine constitutes from about 10 mM to about 250 mM of said gel, and said gel further comprises glycine at a concentration of from about 50 mM to about 500 mM, a conjugate ampholyte at a proportion of from about 20 mole percent to about 60 mole percent relative to said glycine, and a weak acid at a concentration of from about 10 mM to about 500 mM.

53. The method of claim 48 wherein said voltage is at least about 350 volts.

54. The method of claim 48 wherein said voltage is from about 400 volts to about 600 volts.

* * * * *